(12) United States Patent
Gangadharmath et al.

(10) Patent No.: US 9,023,316 B2
(45) Date of Patent: May 5, 2015

(54) SYNTHESIS OF 18F-LABELED TRACERS IN HYDROUS ORGANIC SOLVENTS

(75) Inventors: Umesh Gangadharmath, Los Angeles, CA (US); Joseph Walsh, Pacific Palisades, CA (US); Hartmuth Kolb, Playa Del Rey, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 215 days.

(21) Appl. No.: 13/634,708

(22) PCT Filed: Apr. 8, 2011

(86) PCT No.: PCT/US2011/031681
§ 371 (c)(1),
(2), (4) Date: Sep. 13, 2012

(87) PCT Pub. No.: WO2011/127345
PCT Pub. Date: Oct. 13, 2011

(65) Prior Publication Data
US 2013/0005956 A1  Jan. 3, 2013

Related U.S. Application Data

(60) Provisional application No. 61/322,074, filed on Apr. 8, 2010.

(51) Int. Cl.
*C07B 59/00* (2006.01)
*B01D 15/36* (2006.01)
*A61K 51/04* (2006.01)

(52) U.S. Cl.
CPC .............. *B01D 15/363* (2013.01); *A61K 51/04* (2013.01); *A61K 51/0448* (2013.01); *A61K 51/0453* (2013.01); *A61K 51/0455* (2013.01); *A61K 51/0459* (2013.01); *A61K 51/047* (2013.01); *A61K 51/0491* (2013.01)

(58) Field of Classification Search
None
See application file for complete search history.

(56) References Cited

U.S. PATENT DOCUMENTS

| | | | |
|---|---|---|---|
| 4,606,908 | A | 8/1986 | Bassingthwaighte et al. |
| 5,425,063 | A | 6/1995 | Ferrieri et al. |
| 7,022,872 | B2 | 4/2006 | Walsh et al. |
| 7,160,637 | B2 | 1/2007 | Chiao et al. |
| 7,419,653 | B2 | 9/2008 | Walsh et al. |
| 7,666,392 | B2 | 2/2010 | Kolb et al. |
| 7,807,394 | B2 | 10/2010 | Kolb et al. |
| 7,829,063 | B2 | 11/2010 | Kolb et al. |
| 7,928,210 | B2 | 4/2011 | Kolb et al. |
| 2004/0236085 | A1 | 11/2004 | Luthra et al. |
| 2007/0196271 | A1* | 8/2007 | Mukherjee et al. ......... 424/1.11 |
| 2008/0019906 | A1 | 1/2008 | DiMagno et al. |
| 2008/0170993 | A1 | 7/2008 | Srinivasan et al. |
| 2009/0036668 | A1 | 2/2009 | Elizarov et al. |
| 2009/0076259 | A1* | 3/2009 | Osborn et al. ............... 536/124 |
| 2009/0123372 | A1* | 5/2009 | Kolb et al. .................. 424/1.89 |
| 2010/0074843 | A1 | 3/2010 | Kolb et al. |
| 2010/0196254 | A1 | 8/2010 | Lemaire et al. |
| 2010/0239496 | A1 | 9/2010 | Gangadharmath et al. |
| 2010/0243972 | A1 | 9/2010 | Voccia et al. |
| 2011/0006011 | A1 | 1/2011 | Aerts et al. |
| 2011/0008215 | A1 | 1/2011 | Elizarov et al. |
| 2011/0150714 | A1 | 6/2011 | Elizarov et al. |
| 2011/0182812 | A1 | 7/2011 | Szardenings et al. |

FOREIGN PATENT DOCUMENTS

| | | |
|---|---|---|
| CN | 1887828 | 1/2007 |
| EP | 0588480 | 3/1994 |
| EP | 0798307 | 10/1997 |
| JP | 4077699 | 3/1992 |
| JP | H07-507813 A | 8/1995 |
| JP | 2008-520636 A | 6/2008 |
| WO | 9421653 | 9/1994 |
| WO | 2006065038 | 6/2006 |
| WO | 2008101305 | 8/2008 |
| WO | 2008/124703 A2 | 10/2008 |
| WO | 2009003251 | 1/2009 |
| WO | 2009059977 | 5/2009 |
| WO | 2010/000409 A2 | 1/2010 |
| WO | 2011119565 | 9/2011 |
| WO | 2011127345 | 10/2011 |

OTHER PUBLICATIONS

Joël Aerts et al., "Fast production of highly concentrated reactive [18F] fluoride for aliphatic and aromatic nucleophilic radiolabeling", Tetrahedron Letters, vol. 51, pp. 64-66 (2009).
Hyung Woo Kim et al., "Rapid synthesis of [18F]FDG without an evaporation step using an ionic liquid", Applied Radiation and Isotopes, vol. 61, pp. 1241-1246 (2004).
Dong Wook Kim et al., "A New Class of SN2 Reactions Catalyzed by Protic Solvents: Facile Fluorination for Isotopic Labeling of Diagnostic Molecules", J. Am. Chem. Soc., vol. 128, No. 50, pp. 16394-16397 (Nov. 23, 2006).
Haubner et al., "[18F]Galacto-RGD: Synthesis, Radiolabeling, Metabolic Stability, and Radiation Dose", Bioconjugate Chem. 2004, 15, 61-69.
Lemaire, et al., "Fast Production of Highly Reactive No-Carrier-Added [18F] Fluoride for the Labeling of Radiopharmaceuticals", In Angewandte Chemie (International Ed. In English) vol. 49, No. 18, 25 Mar. 2010, pp. 3161-3164.

(Continued)

*Primary Examiner* — Layla Bland
(74) *Attorney, Agent, or Firm* — Peter Kendall

(57) ABSTRACT

A method for synthesizing an $^{18}$F-labeled probe. The method includes a step of eluting an amount of $^{18}$F with a first solvent which includes a predetermined amount of water and at least one organic solvent. In this step, the $^{18}$F elutes as an $^{18}$F solution. The method also includes a step of using the $^{18}$F solution to perform $^{18}$F-labeling in the presence of at least one labeling reagent and at least one phase transfer catalyst so as to generate the $^{18}$F-labeled probe. In the method, there is no step of drying the $^{18}$F starting from a time when the eluting step is performed and ending at a time when the $^{18}$F-labeling step is performed.

16 Claims, 8 Drawing Sheets

(56) References Cited

OTHER PUBLICATIONS

Cogneau, et al., "Production of a High Purity <18>F Radioactive Beam", In Nuclear Instruments and Methods in Physics Research, Section A-Accelerators, Spectrometers, Detectors and Associated Equipment. vol. 420, No. 3, Jan. 11, 1999, pp. 489-493.

S. John Gatley., "Rapid Production and Trapping of [<18>F]Fluorotrimethylsilane, and Its Use in Nucleophilic Fluorine-18 Labeling Without an Aqueous Evaporation Step", In Applied Radiation and Isotopes, International Journal of Radiation Applications and Instrumentation, Part A, vol. 40, No. 6, 1 Jan. 1989, pp. 541-544.

PCT Search Report dated Jun. 6, 2011 in PCT/US2011/031681.

Muller, P., "Glossary of terms used in physical organic chemistry", IUPAC Pure & Appl. Chem. (1994) 66(5): 1077-1084.

Jewett et al., "Extraction of [18F]Fluoride from [18O]Water by a Fast Fibrous Anion Exchange Resin", Appl. Radiat. Isot. vol. 41, No. 6, pp. 583-586 (1990).

Mukhopadhyay et al., "Radiosynthesis of 2'-deoxy-[18F]-fluoro-5-methyl-1-β-L-arabinofuranosyluracil ([18F]-L-FMAU) for PET", Applied Radiation and Isotopes (2007) 65:941-946.

Vasdev, et al., "Syntheses and in vitroevaluation of fluorinated naphthoxazines as dopamine D2/D3 receptor agonists: radiosynthesis, ex vivo biodistribution and autoradiography of [18F]F-PHNO", Nuclear Medicine and Biology, vol. 34, Issue 2, Feb. 2007, pp. 195-203.

Coenen, et al., "Preparation of N.C.A. [17-18F]-fluoroheptadecanoic acid in high yields via aminopolyether supported, nucleophilic fluorination", Journal of Labelled Compounds and Radiopharmaceuticals, vol. 23, Issue 5, pp. 455-466 (1986).

Alexoff, et al., "Recovery of [18F]fluoride from [18O]water in an electrochemical cell", International Journal of Radiation Applications and Instrumentation. Part A. Applied Radiation and Isotopes, vol. 40, Issue 1, 1989, pp. 1-6.

Office Action dated Apr. 3, 2014 in Japanese Patent Application No. 2013-503976.

* cited by examiner

| Reg | (mm) Start | (mm) Stop | (mm) Centroid | RF | Region Counts | Region CPM | % of Total | % of ROI |
|---|---|---|---|---|---|---|---|---|
| Rgn 1 | 55.1 | 65.6 | 60.1 | 0.002 | 1847.5 | 1847.5 | 2.41 | 2.53 |
| Rgn 2 | 83.9 | 96.1 | 89.5 | 0.369 | 43531.7 | 43531.7 | 56.89 | 59.72 |
| Rgn 3 | 104.8 | 111.8 | 108.0 | 0.600 | 764.8 | 764.8 | 1.00 | 1.05 |
| Rgn 4 | 117.0 | 128.4 | 122.0 | 0.775 | 26744.3 | 26744.3 | 34.95 | 36.69 |
| 4 Peaks | | | | | 72888.4 | 72888.4 | 95.26 | 100.00 |

SYNTHESIS OF 18F-LABELED TRACERS IN HYDROUS ORGANIC SOLVENTS

This application is the U.S. national phase application of PCT International Application No. PCT/US2011/31681, filed on Apr. 8, 2011, which claims priority to U.S. Provisional Patent Application No. 61/322,074 filed on Apr. 8, 2010, the disclosure of which is incorporated herein by reference in its entirety.

BACKGROUND OF THE INVENTION

1. Field of the Invention

The present invention relates to synthesis of $^{18}$F-labeled probes for positron emission tomography ("PET"). More specifically, a method of synthesizing $^{18}$F-labeled probes is disclosed, where a solvent with a predetermined amount of water in at least one organic solvent is used to a) elute the $^{18}$F-fluoride from an anion exchange cartridge and b) perform the $^{18}$F-labeling, without drying the $^{18}$F-fluoride, in the presence of at least one labeling reagent and at least one phase transfer catalyst.

2. Description of Related Art

Synthesis of $^{18}$F-labeled probes for positron emission tomography ("PET") has increased tremendously over the last 10 years as there is a growing demand for radiopharmaceuticals that successfully detect aberrant biochemical functions in vivo. The unique physiochemical properties of PET tracers make them ideally suited for several imaging applications such as the early detection and staging of diseases, treatment monitoring and stratification of patients who may or may not respond to a particular therapy.

The synthesis of these radiolabeled molecules is undoubtedly time consuming, labor intensive and randomly unreliable. In an effort to minimize these production issues, radiochemists have attempted to reduce the labeling procedures to their simplest, quickest and most reliable protocols. Despite these process improvements, the radiolabeling processes still contain inherent inefficiencies that would benefit from further chemistry and process improvements.

The conventional means for $^{18}$F-labeling involves the formation of "activated" or "naked" fluoride, i.e. fluoride that is sufficiently moisture-free and thus suitable for radiolabeling. It is widely known that the desolvation of fluoride increases its nucleophilic character. See V. M. Vlasov, "Fluoride ion as a nucleophile and a leaving group in aromatic nucleophilic substitution reactions", J. of Fluorine Chem., vol. 61, pp. 193-216 (1993). In these conventional labeling protocols, trace amounts of $^{18}$F-fluoride are sequestered onto an anion exchange column from several milliliters of $^{18}$O-water. Afterwards, the $^{18}$F-fluoride ion is eluted from the anion exchange column through the use of salts, such as $K_2CO_3$, dissolved in water. An additive such as the potassium crown ether Kryptofix K222, which is dissolved in anhydrous acetonitrile, may be used in conjunction with aqueous $K_2CO_3$ to facilitate the elution of $^{18}$F-fluoride, or optionally added into the reaction vessel after the $K_2CO_3$-mediate elution. After the elution step, there is an extensive drying protocol needed as reagents $K_2CO_3$ and Kryptofix K222 are in a highly hydrous solution of acetonitrile. This drying step generates an activated mixture of $K_2CO_3$, Kryptofix K222 and $^{18}$F-fluoride. The drying process begins by evaporating the azeotropic mixture at elevated temperatures, oftentimes at reduced pressures to aid in the evaporation of water from the reaction vessel. This initial drying can take up to 30 minutes to complete, depending on the efficiency of drying. After the first evaporation, it may be necessary to perform additional evaporations to effectively remove of enough water to render the $^{18}$F-fluoride sufficiently moisture-free for labeling.

There are several inherent problems with this approach to generating activate reagents for $^{18}$F-fluorination. First, the amount of water present after the initial drying step will vary from run to run given mechanical differences in vacuum, gas flows, valve integrity and temperature control. Any single mechanical problem, or combination thereof, will negatively impact the efficiency of drying and hence, the labeling results. Since the amount of residual water could vary greatly from run to run, the radiolabeling results would then be inconsistent, making reliable production of radiotracers difficult. Also, given the time needed to successfully dry the fluoride, a good portion of the total synthesis time is dedicated to the drying step. Lastly, because of the concern of residual water in the reaction, there is a potential for operators to "overdry" the reaction mixture prior to fluorination. In this instance, drying the reagents for too long may be as equally hurtful as under-drying the reagents (under-drying being the failure to remove sufficient moisture from the reagents for $^{18}$F-fluorination). For example, Kryptofix K222 decomposition is directly related to drying times and temperatures: prolonged drying at high temperature compromises the integrity and functionality of Kryptofix K222. To address these issues, a method that minimizes the length of drying and can accurately control the amount of moisture from run to run would be a substantial improvement to current radiolabeling practices.

Alternate methods have been developed in an attempt to obviate the need for the drying step that either elute $^{18}$F-fluoride from anion exchange resins using additives in either anhydrous organic solvents (such as acetonitrile, see Joël Aerts et al., "Fast production of highly concentrated reactive [$^{18}$F] fluoride for aliphatic and aromatic nucleophilic radiolabeling", Tetrahedron Letters, vol. 51, pp. 64-66 (2009); International Patent Application Pub. No. WO 2009/003251) or by using ionic liquids in hydrous acetonitrile (Hyung Woo Kim et al., "Rapid synthesis of [$^{18}$F]FDG without an evaporation step using an ionic liquid", Applied Radiation and Isotopes, vol. 61, pp. 1241-1246 (2004)). For these types of elutions using compounds with unknown toxicities, one would want to assay for these additives in the final product prior to injection and imaging, which ultimately complicates the production workflow.

The use of hydroalcoholic (i.e. protic solvents) co-mixtures is reported to improve $^{18}$F-labeling yields over the standard single solvent $^{18}$F-labeling conditions. Dong Wook Kim et al., "A New Class of $S_N2$ Reactions Catalyzed by Protic Solvents: Facile Fluorination for Isotopic Labeling of Diagnostic Molecules", J. Am. Chem. Soc., vol. 128, no. 50, pp. 16394-16397 (Nov. 23, 2006). While the increases in yields are believed to be a result of the unique interactions between the $^{18}$F-fluoride and possibly the leaving group on the precursor, it is not practical to use hydroalcoholic solvents, such as t-amyl alcohol, as they must be analyzed in the final product. Additionally, the low polarity of these bulky solvents can hinder the precursor's solubility which can be used for the labeling reaction, thus negatively impacting the radiolabeling yield.

SUMMARY OF THE INVENTION

An ideal process for labeling would include an additive that benefits the labeling yields, requires no additional testing beyond what is currently in place for tracer production, eliminates the need for the drying step and allows for the precise amount of water to be present in each reaction for every run.

With this in mind, one embodiment of the current inventions includes a method for synthesizing an $^{18}$F-labeled probe. The method includes a step of eluting an amount of $^{18}$F with a first solvent which includes a predetermined amount of water and at least one organic solvent. In this step, the $^{18}$F elutes as an $^{18}$F solution. The method also includes a step of using the $^{18}$F solution to perform $^{18}$F-labeling in the presence of at least one labeling reagent and at least one phase transfer catalyst so as to generate the $^{18}$F-labeled probe. In the method, there is no step of drying the $^{18}$F starting from a time when the eluting step is performed and ending at a time when the $^{18}$F-labeling step is performed.

A solution for use in synthesizing an $^{18}$F-labeled probe is also provided. The solution includes an amount of $^{18}$F, water, and at least one organic solvent. The total amount of water in this solution is in a range of about 0.1% to about 5.0%. The solution may also include at least one labeling reagent, and at least one phase transfer catalyst. In addition, the solution may include a probe precursor, and have a total amount of water in a range of about 0.1% to about 2.0%.

DETAILED DESCRIPTION OF EMBODIMENTS

Figure 1:
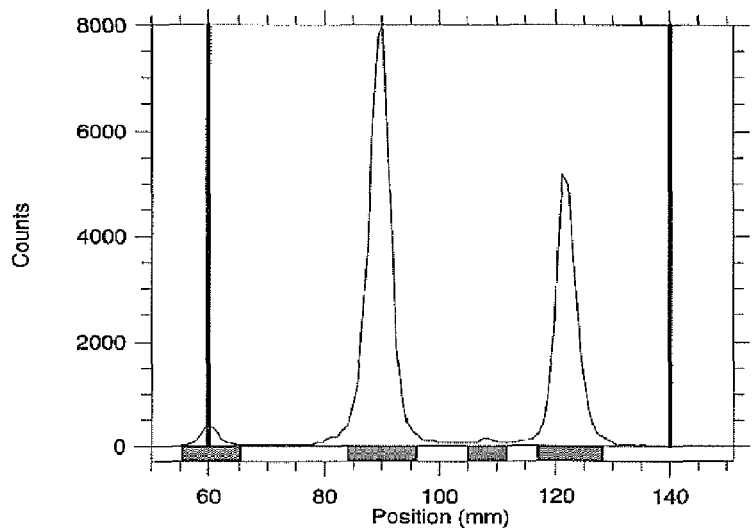
FIG. 1 shows an example of fluorodeoxyglucose ($^{18}$F) ("FDG" or "$^{18}$F-FDG") synthesis (run number 1) radio thin layer chromatography ("Radio-TLC") of the crude product after fluorination. Rgn 1 is $^{18}$F-fluoride, Rgn 2 is $^{18}$F-FDG, Rgn 3 is an unknown $^{18}$F-labeled by-product, Rgn 4 is tetra-acetyl $^{18}$F-FDG.

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

In this invention, $^{18}$F-labeling occurs in high yields with precisely controlled amounts of water without the use of a lengthy drying step. More specifically, a solvent of a predetermined amount of water in at least one organic solvent is used to a) elute the $^{18}$F-fluoride from an anion exchange resin and b) perform the $^{18}$F-labeling, without drying the $^{18}$F-fluoride, in the presence of at least one labeling reagent and at least one phase transfer catalyst. Any suitable labeling reagents and phase transfer catalysts may be used. Examples of appropriate labeling reagents include, $K_2CO_3$, $KHCO_3$, $Cs_2CO_3$, potassium mesylate, potassium oxylate, and tetrabutylammonium bicarbonate, An example of a suitable phase transfer catalyst includes Kryptofix K222. The organic solvent may include a polar aprotic solvent, such as, for example, acetonitrile, dimethyl sulfoxide ("DMSO"), tetrahydrofuran ("THF"), dimethylformamide ("DMF"), N-methylpyrrolidone ("NMP"), and dioxane, as well as others. The organic solvent may also include a polar protic solvent, such as, for example, tBuOH and t-amyl alcohol, as well as others.

The amount of water as a percentage of the total solvent may range from about 0.1% to about 2%. Water, for elution from the anion exchange cartridge however, may range from about 0.1% to about 5%. The amount of base (e.g., $K_2CO_3$) may be about 0.1 to about 50 mg/mL. Because the amount of water is controlled by the elution of fluoride, the percentage of water remains the same from run to run, making the radiochemistry more consistent. Also, because the fluorination appears to tolerate the presence of a small range of water, there is no need to dry the fluoride. As a beneficial consequence of eliminating the drying step, the decomposition of temperature-sensitive reagents such as Kryptofix K222 and tetrabutylammonium bicarbonate ("TBAB") are minimized. Additionally, the reactions are completed in a shorter period of time, leading to higher yields and more usable product in-hand. There is less mechanical wear on the instrument, since a portion of mechanical system is no longer used for drying. Unlike losses of radioactivity commonly reported as a consequence of drying $^{18}$F-fluoride, this method would not suffer from this type of radioactivity loss. Lastly, there are fewer chances of labeling failures due to a consistent amount of water always present in every reaction.

Examples of $^{18}$F-labeled PET probes that can be generated by the method of the present invention include, but are not limited to, [$^{18}$F]-3-Fluoro-2-(4-((2-nitro-1H-imidazol-1-yl)methyl)-1H-1,2,3-triazol-1-yl)propan-1-ol ("HX4" or "$^{18}$F-HX4"), fluorodeoxythymidine ("FLT"), 1-[$^{18}$F]fluoro-3-(2-nitro-1H-imidazol-1-yl)propan-2-ol ("F-MISO"), [$^{18}$F]-fluoroazomycinarabinofuranoside ("FAZA"), 5-[3-($^{18}$F)fluoropropyl]-2,3-dimethoxy-N-{[(2S)-1-(prop-2-en-1-yl)pyrrolidin-2-yl]methyl}benzamide ("Fallypride"), 9-(4-[$^{18}$F]Fluoro-3-hydroxymethylbutyl)guanine ("FHBG"), 9-[(3-[$^{18}$F]-fluoro-1-hydroxy-2-propoxy)methyl]guanine ("FHPG"), ($^{18}$F)fluoroethyl azide, $^{18}$F-4-fluorobenzaldehyde, $^{18}$F-4-fluoroethylbenzoate, $^{18}$F-4-fluoromethyl benzoate, and 7-Methoxy-2 (6-[$^{18}$F]fluoropyridin-3-yl)imidazo[2,1-b]-8-pyridinothiazole ("$^{18}$F-W372"). Other examples of $^{18}$F-labeled PET probes that can be generated by the method of the present invention include, but are not limited to, 2'-Deoxy-2'-[$^{18}$F]fluoro-5-fluoro-1-β-D-arabinofuranosyluracil ("FFAU"), as well as the compounds listed in the table below:

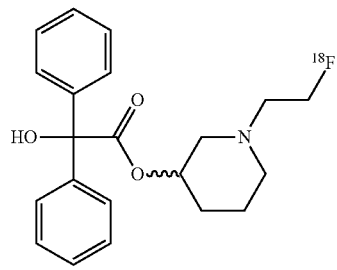 [SMILES: O=C(OC1CCCN(CC[18F])C1)C(O)(c1ccccc1)c1ccccc1]
1-[2-($^{18}$F)fluoroethyl]
piperidin-3-yl
hydroxy(diphenyl)acetate
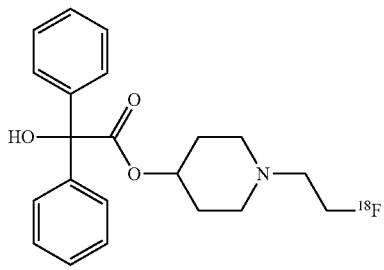 [SMILES: O=C(OC1CCN(CC[18F])CC1)C(O)(c1ccccc1)c1ccccc1]
1-[2-($^{18}$F)fluoroethyl]
piperidin-4-yl
hydroxy(diphenyl)acetate
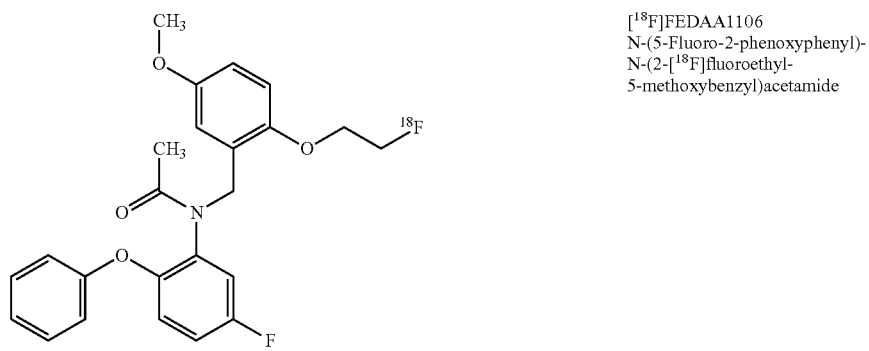
[$^{18}$F]FEDAA1106
N-(5-Fluoro-2-phenoxyphenyl)-
N-(2-[$^{18}$F]fluoroethyl-
5-methoxybenzyl)acetamide
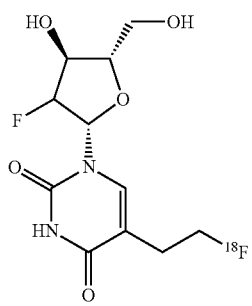 [SMILES: O=c1[nH]c(=O)n([C@H]2O[C@@H](CO)[C@H](O)C2F)cc1CC[18F]]
1-(2-deoxy-2-fluoro-β-D-
arabinofuranosyl)-5-[2-
($^{18}$F)fluoroethyl]pyrimidine-
2,4(1H,3H)-dione
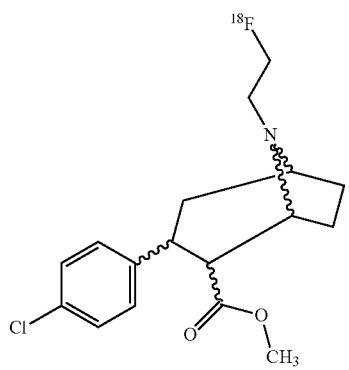
[$^{18}$F]FECNT
2-Carbomethoxy-3-(4-
chlorophenyl)-8-(2-
[$^{18}$F]fluoroethyl)nortropane -continued
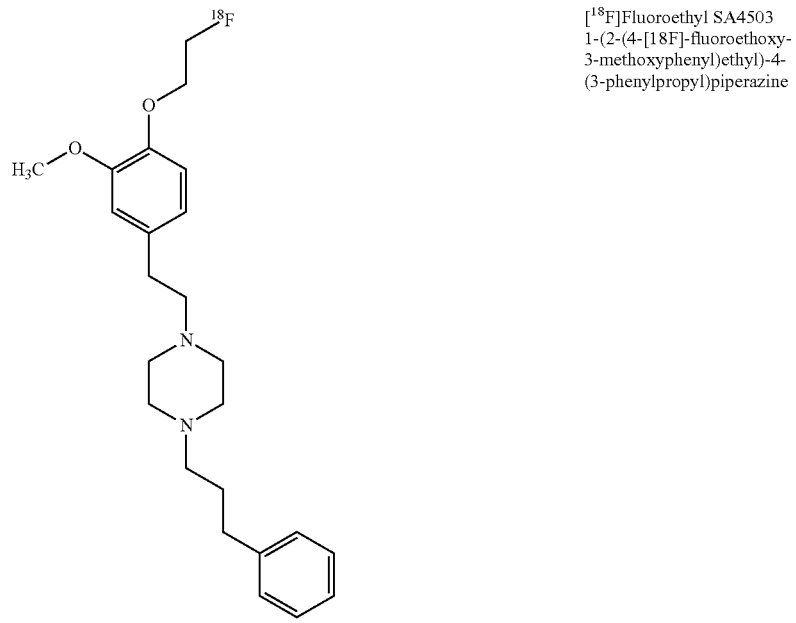
[18F]Fluoroethyl SA4503
1-(2-(4-[18F]-fluoroethoxy-3-methoxyphenyl)ethyl)-4-(3-phenylpropyl)piperazine
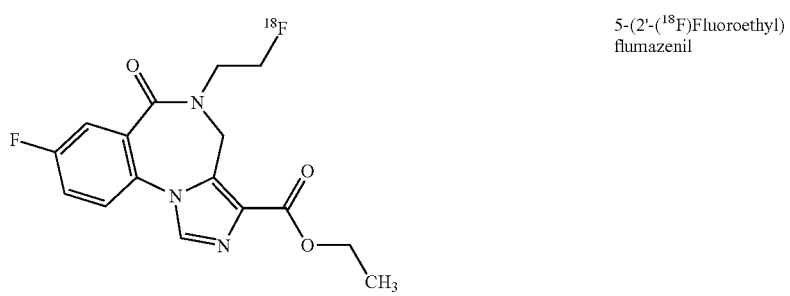
5-(2'-(18F)Fluoroethyl) flumazenil
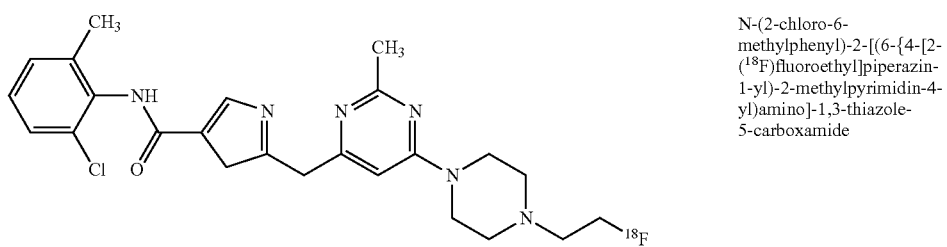
N-(2-chloro-6-methylphenyl)-2-[(6-{4-[2-(18F)fluoroethyl]piperazin-1-yl)-2-methylpyrimidin-4-yl)amino]-1,3-thiazole-5-carboxamide
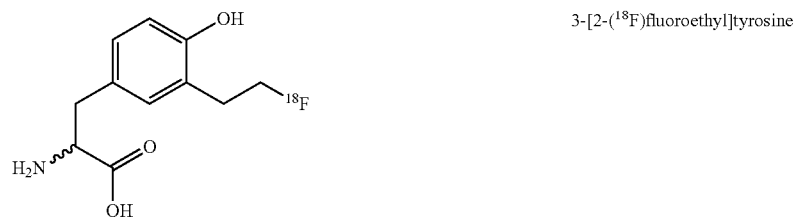
3-[2-(18F)fluoroethyl]tyrosine
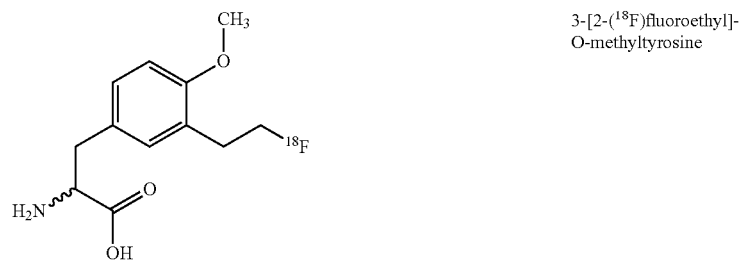
3-[2-(18F)fluoroethyl]-O-methyltyrosine

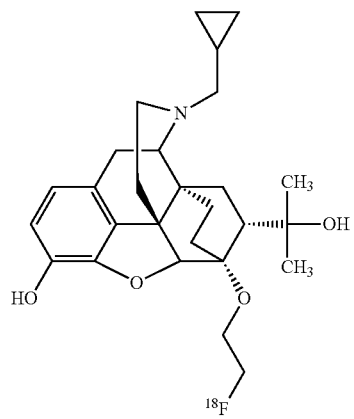 [SMILES: CC(C)(O)[C@H]1C[C@@]23CC[C@]1(OCC[18F])C1Oc4c(O)ccc5c4[C@@]12CCN(CC1CC1)C3C5]

[18F]FDPN
6-O-(2-[18F]fluoroethyl)-
6-O-desmethyldiprenorphine

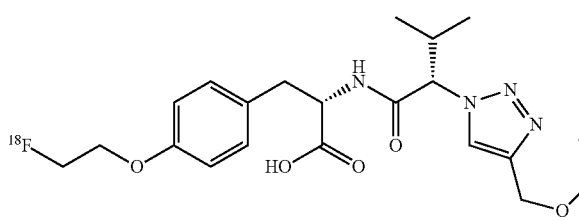

[18F]VM4-037
18F-(S)-3-(4-(2-fluoroethoxy)
phenyl)-2-(3-methyl-2-(4-((2-
sulfamoylbenzo[d]thiazol-
6-yloxy)methyl)-1H-1,2,3-
triazol-1-yl)butanamido)
propanoic acid

VM4037A

Without intention of being bound by a particular mechanism or theory, the $^{18}$F-fluoride anion may displace a leaving group, which may include, but is not limited to, tosylates, mesylates, triflates, nosylates, brosylates, trialkylammonium salts, sulfonate esters, halogens and nitro-groups with $^{18}$F-fluoride in solvents containing the presence of about 0.1% to about 2.0% water.

In general, the process for generating the $^{18}$F-labeled probe includes loading an amount of $^{18}$F onto an anion exchange cartridge. By anion exchange cartridge, what is meant is any vessel containing any convenient anion exchange resin or other material suitable for adsorbing $^{18}$F. The $^{18}$F loaded on the anion exchange resin is then prepared for elution. This preparation may include washing the cartridge with an organic solvent (e.g., anhydrous acetonitrile) and then drying the cartridge (e.g., by passing an inert gas through the cartridge.

Next the $^{18}$F is eluted from the cartridge, for example by passing a solution including water, an organic solvent, a labeling reagent, and a phase transfer catalyst through the cartridge so as to obtain an $^{18}$F solution containing $^{18}$F, water, the organic solvent, the labeling reagent, and the phase transfer catalyst. At this point the amount of water in the $^{18}$F solution may range from 0.1% to 5.0%. A probe precursor is then combined with the $^{18}$F solution so as to arrive at an $^{18}$F-labeling solution which has water in an amount of from 0.1% to 2.0%. This can be accomplished, for example, by diluting either the probe precursor or the $^{18}$F solution, or both, with an appropriate amount of organic solvent. Accordingly, it is possible to generate the $^{18}$F-labeling solution without any drying of the eluted $^{18}$F solution.

While the $^{18}$F-labeling solution should contain water in an amount of from 0.1% to 2.0%, it is preferable for the water to be in an amount of from 0.5% to 1.5%, and more preferable for the water to be in an amount of around 1.0%.

Examples

Summary of Labeling Results

| Entry | Tracer | % H$_2$O for QMA elution | H$_2$O in 0.4 mL for QMA elution (vol) | MeCN added (vol) | % H$_2$O total for labeling | % conversion (intermediate) determined by RadioTLC | % conversion (product) determined by RadioTLC |
|---|---|---|---|---|---|---|---|
| 1 | FDG | 5% | 20 uL | 1.6 mL | 1% | >95% | NA |
| 2 | FDG | 5% | 20 uL | 1.6 mL | 1% | >95% | NA |
| 3 | FDG | 25% | 100 uL | 1.6 mL | 5% | 0% | NA |
| 4 | FDG | 5% | 20 uL | 1.6 mL | 1% | NA | 60% (isolated yield) |
| 5 | FLT | 5% | 20 uL | 1.6 mL | 1% | >90% | >93%** |
| 6 | HX4 | 5% | 20 uL | 1.6 mL | 1% | >90% | NA |
| 7 | HX4 | 5% | 20 uL | 1.6 mL | 1% | >90%** | >70%** |

**Denotes analysis performed by Radio-HPLC

Preparation of the K₂CO₃ and Kryptofix K222 Elution Solvent:

K₂CO₃ (11 mg) was dissolved in water (0.1 mL). Kryptofix K222 (100 mg) was dissolved in acetonitrile (1.9 mL). The solutions were mixed and 0.4 mL, or 2×0.2 mL, was used to elute ¹⁸F-fluoride from an anion exchange cartridge.

Loading and Drying of the Anion Exchange Cartridge:

An activated anion exchange cartridge (QMA lite, bicarbonate form), was loaded with ¹⁸F-fluoride in ¹⁸O-water. The cartridge was then washed with anhydrous acetonitrile (3×1 mL) to remove residual moisture from the cartridge. The cartridge was then further dried by passing an inert gas (such as He) through the cartridge for approximately 30 to 90 seconds.

Elution of ¹⁸F-Fluoride from the Anion Exchange Cartridge:

After a solution of ¹⁸F-fluoride (up to 50 mCi per run) in ¹⁸O-water was passed through the ion-exchange column, a solution of K₂CO₃/Kryptofix K222 (0.4 mL or 2×0.2 mL) was passed through the anion exchange cartridge into a dried reaction vessel. An additional portion of anhydrous acetonitrile (0.6 mL) was added to the reaction vessel. This final step constitutes the formation of ¹⁸F-fluoride in a hydrous organic solution that was suitable for radiolabeling.

Synthesis of ¹⁸F-FDG (Entries 1, 2 and 3):

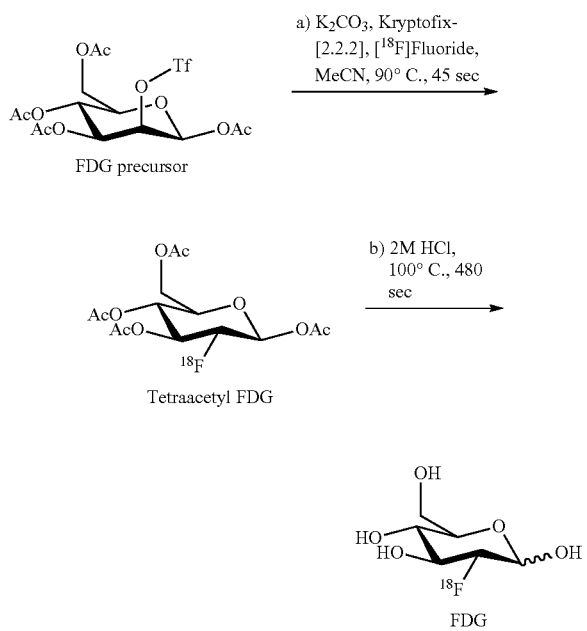

Figure 2:
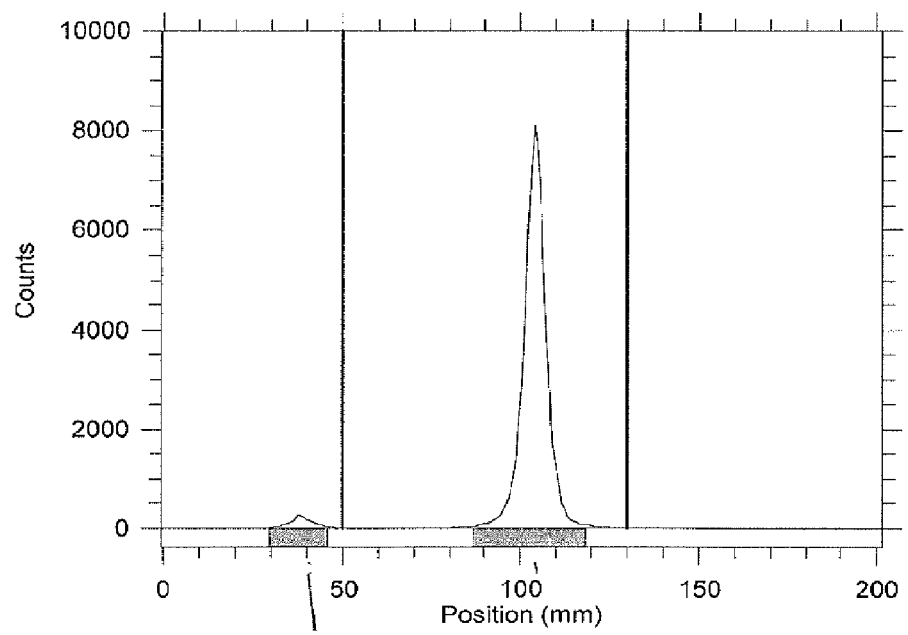
FIG. 2 shows an example of $^{18}$F-FDG synthesis (run number 2) Radio-TLC of the crude product after fluorination. Rgn 1 is $^{18}$F-fluoride, Rgn 2 is tetra-acetyl $^{18}$F-FDG.

Fluorodeoxyglucose (¹⁸F) ("FDG" or "¹⁸F-FDG") precursor (mannose triflate, 50 mg) dissolved in acetonitrile (1.0 mL) was added to the reaction vessel containing the activated ¹⁸F-fluoride. The reaction is heated at 90° C. for 45 seconds. Radio thin layer chromatography ("Radio-TLC") indicated that the percent conversion of ¹⁸F-fluoride to ¹⁸F-FDG tetraacetate plus ¹⁸F-FDG was >95% (FIG. 1). This reaction sequence was repeated a second time and the percent conversion of ¹⁸F-fluoride to ¹⁸F-FDG tetraacetate plus ¹⁸F-FDG was >95% (FIG. 2). When the labeling was performed in a solution containing 5% water (Entry 3), no labeling was observed.

Synthesis of ¹⁸F-FDG (Entry 4):

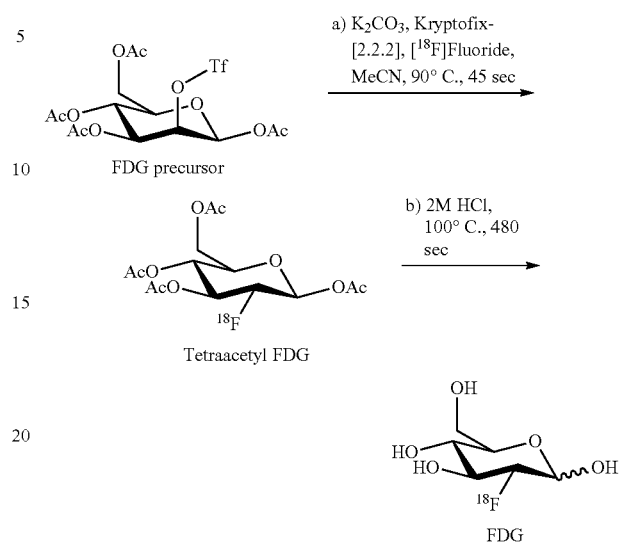

Figure 3:
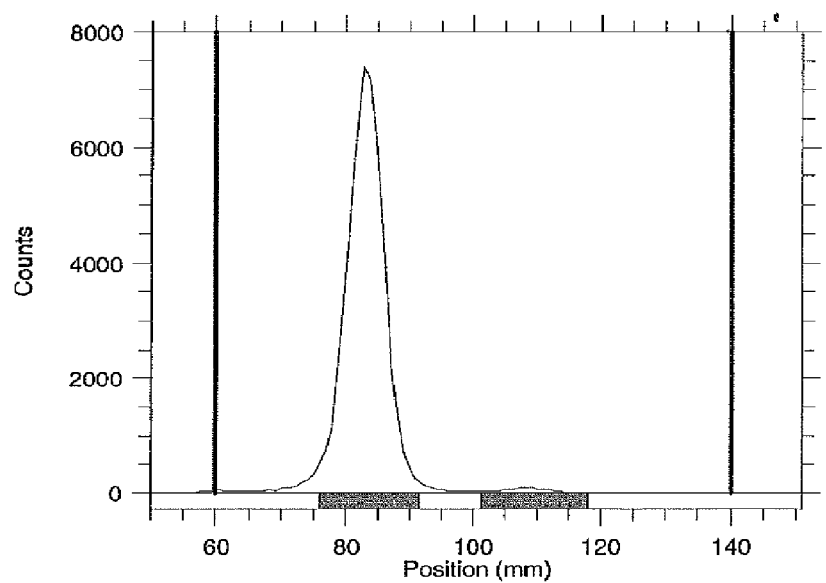
FIG. 3 shows an example of Radio-TLC of the purified $^{18}$F-FDG as measured by Radio-TLC. The purity of $^{18}$F-FDG is greater than 98%.

FDG precursor (mannose triflate, 50 mg) dissolved in acetonitrile (1.0 mL) was added to the reaction vessel containing the activated ¹⁸F-fluoride (985 mCi). The reaction is heated at 90° C. for 45 seconds. The MeCN was removed under reduced pressure and heat. HCl (2M, 1 mL) was added and the reaction was heated at 100° C. for 480 seconds. The crude reaction mixture was diluted with water and passed through a series of cartridges (Al2O3, C18, ICH—HCO₃) to afford 445 mCi (60% yield, decay corrected) 65 minutes after EOB. Radio-TLC indicated that purity of ¹⁸F-FDG was >95% (FIG. 3).

Synthesis of ¹⁸F-FLT (Entry 5):

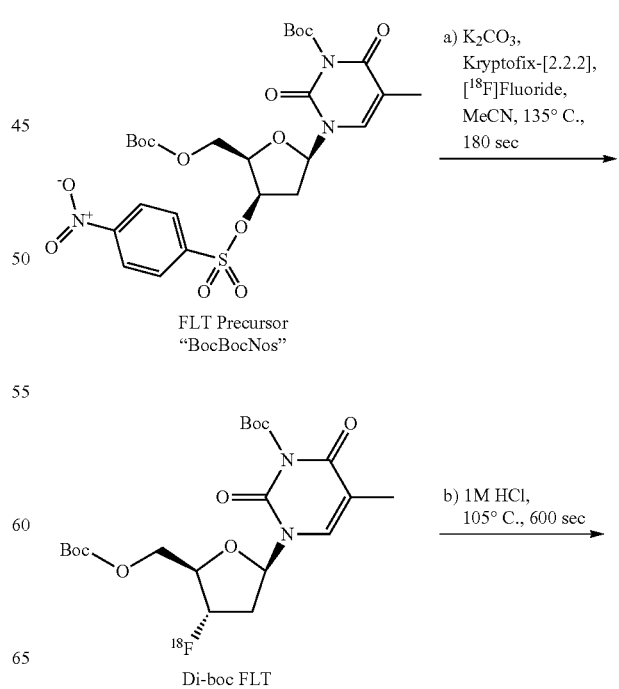

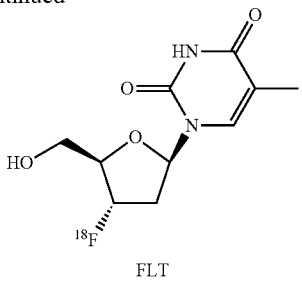

FLT

Figure 4:
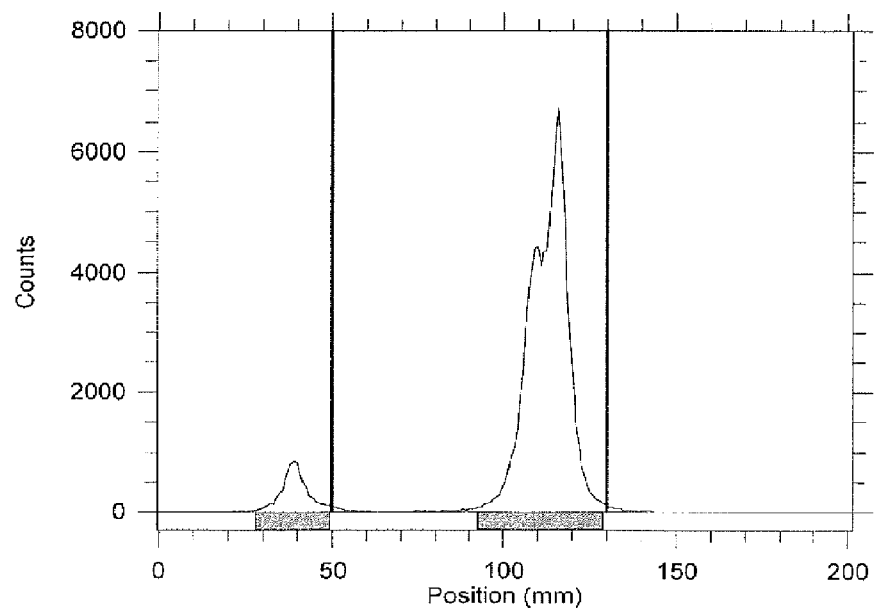
FIG. 4 shows an example of [$^{18}$F]-fluorodeoxythymidine ("$^{18}$F-FLT") synthesis, Radio-TLC of the crude product after fluorination. Rgn 1 is $^{18}$F-fluoride, Rgn 2 is Bis-Boc $^{18}$F-FLT.
Figure 5:
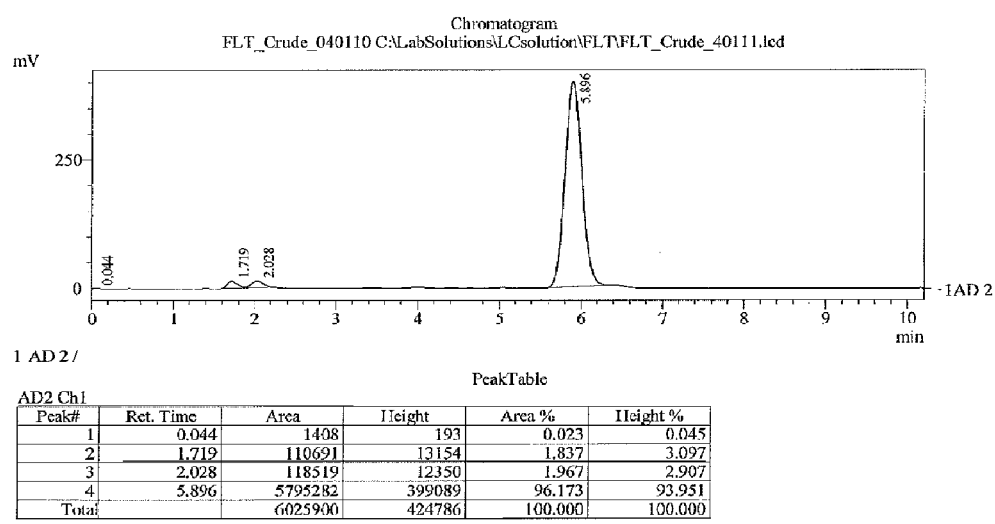
FIG. 5 shows an example of $^{18}$F-FLT synthesis, radio high-pressure liquid chromatography ("Radio-HPLC") of the crude product after hydrolysis. Peaks 2 and 3 are $^{18}$F-fluoride, Peak 4 is $^{18}$F-FLT.

Fluorodeoxythymidine ($^{18}$F) ("FLT" or "$^{18}$F-FLT") precursor (Boc-Boc-Nos, 18.5±1.5 mg) dissolved in Acetonitrile (1.0 mL) is added to the reaction vessel. The reaction is heated at 135° C. for 3 min. Radio-TLC indicated that the percent conversion of $^{18}$F-fluoride to $^{18}$F-Di-Boc FLT was >90% (FIG. 4). The MeCN was removed under reduced pressure and heat. The crude material was subjected to deprotection conditions (HCl, 1N, 105° C. for 5 min). HPLC analytical analysis (10% EtOH:water) reveals the presence of $^{18}$F-FLT with a purity of greater than 96% (FIG. 5).

Synthesis of $^{18}$F-HX4 acetate and $^{18}$F-HX4 (Entries 6 and 7):

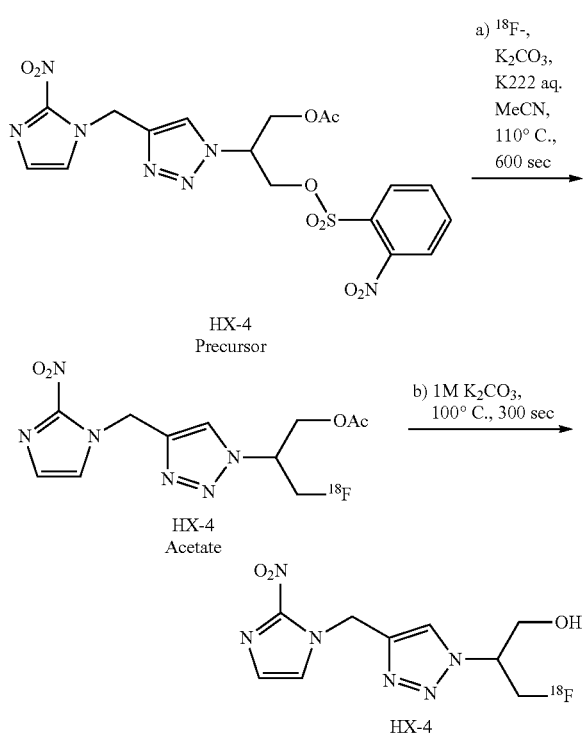

Figure 6:
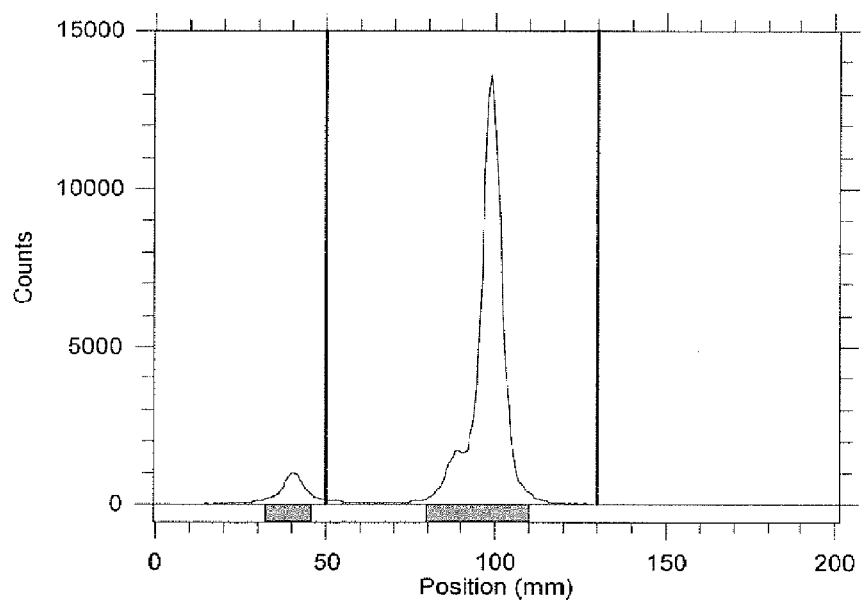
FIG. 6 shows [$^{18}$F]-3-Fluoro-2-(4-((2-nitro-1H-imidazol-1-yl)methyl)-1H-1,2,3-triazol-1-yl)propan-1-ol ("$^{18}$F-HX4") synthesis, Radio-HPLC of the crude product after hydrolysis. Peak 1 is $^{18}$F-fluoride, Peak 2 is a mixture of $^{18}$F-HX4 and $^{18}$F-HX4-acetate.
Figure 7:
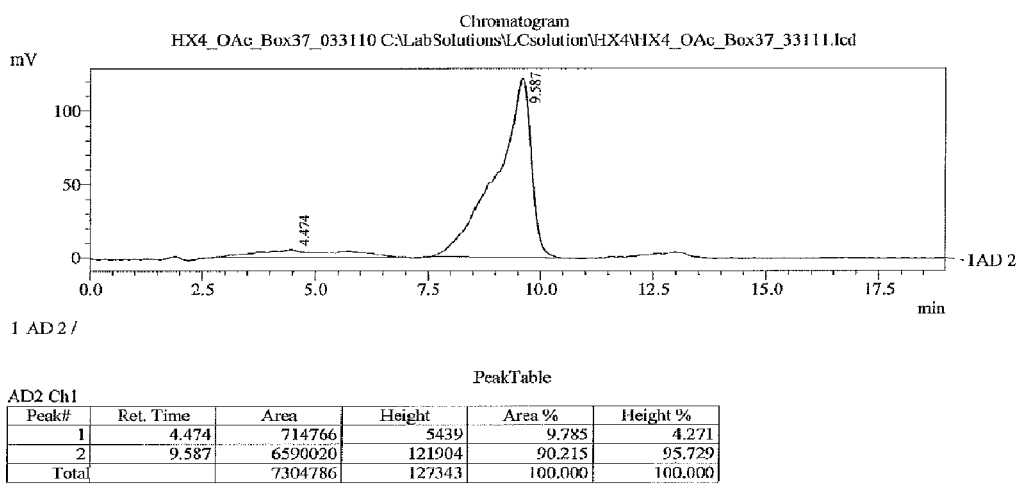
FIG. 7 shows $^{18}$F-HX4 synthesis, Radio-HPLC of the crude product after $^{18}$F-fluorination. Peak 1 is $^{18}$F-fluoride, Peak 2 is $^{18}$F-HX4-OAc.
Figure 8:
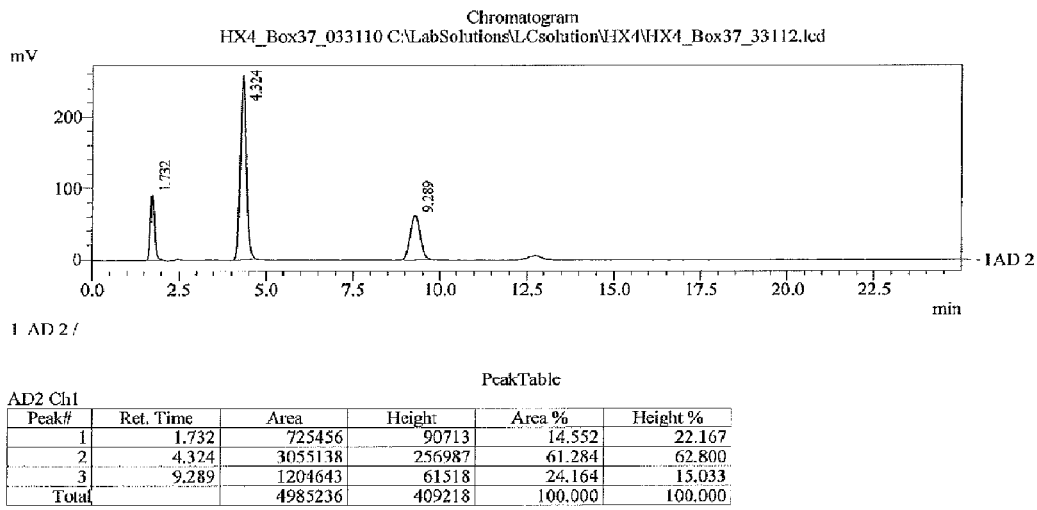
FIG. 8 shows $^{18}$F-HX4 synthesis, Radio-HPLC of the crude product after deprotection. Peak 1 is $^{18}$F-fluoride generated by radiolysis, Peak 2 is $^{18}$F-HX4 and Peak 3 is $^{18}$F-HX4-OAc. Peak 1 was not considered in calculating the conversion of $^{18}$F-HX4-OAc into $^{18}$F-HX4.

[$^{18}$F]-3-Fluoro-2-(4-((2-nitro-1H-imidazol-1-yl)methyl)-1H-1,2,3-triazol-1-yl)propan-1-ol ("HX4" of "$^{18}$F-HX4") precursor (18.5±1.5 mg) dissolved in Acetonitrile (1.0 mL) is added to the reaction vessel. The reaction is heated at 110° C. for 10 min. Radio-TLC indicated that the percent conversion of $^{18}$F-fluoride to $^{18}$F-HX4 and $^{18}$F-HX4 acetate was >90% (FIG. 6). In a second run, the reaction was repeated and the labeling efficiency was monitored by RadioHPLC. After the fluorination step, >90% of the $^{18}$F-fluoride was converted into the labeled intermediate $^{18}$F-HX4-OAc (FIG. 7). The MeCN was removed under reduced pressure and heat. The mixture was further heated with K$_2$CO$_3$ (1M) at 100 C for 300 seconds to complete the deprotection step. The conversion of $^{18}$F-HX4-OAc into $^{18}$F-HX4 was determined to be greater than 70% by radioHPLC (FIG. 8).

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. A variety of modifications to the embodiments described will be apparent to those skilled in the art from the disclosure provided herein. Thus, the present invention may be embodied in other specific forms without departing from the spirit or essential attributes thereof. Various changes may be made without departing from the spirit and scope of the inventions as defined in the following claims.

What is claimed is:

1. A method for synthesizing an $^{18}$F-labeled probe the method comprising:
    (1) eluting an amount of $^{18}$F with a first solvent comprising a predetermined amount of water and at least one organic polar aprotic solvent, but no organic erotic solvents, the $^{18}$F eluting as an $^{18}$F solution, the predetermined amount of water being in a range of about 0.1 vol % to about 5.0 vol %; and
    (2) using the $^{18}$F solution to perform $^{18}$F-labeling in the presence of at least one labeling reagent and at least one phase transfer catalyst so as to generate the $^{18}$F-labeled probe;
    wherein the at least one labeling reagent comprises K$_2$CO$_3$, KHCO$_3$, Cs$_2$CO$_3$, potassium mesylate, potassium oxylate, or tetrabutylammonium bicarbonate;
    wherein the water content of the $^{18}$F solution during $^{18}$F-labeling is in a range of about 0.1 vol % to about 2.0 vol %; and
    wherein there is no step of drying the $^{18}$F solution starting from a time when the eluting is performed and ending at a time when the $^{18}$F-labeling is performed.

2. The method of claim 1, wherein the first solvent further comprises the at least one labeling reagent and the at least one phase transfer catalyst.

3. The method of claim 1, wherein the $^{18}$F-labeling step includes combining the $^{18}$F solution with a probe precursor so as to arrive at an $^{18}$F-labeling solution with the total amount of water in a range of about 0.1 vol % to about 2.0 vol %.

4. The method of claim 3, wherein the $^{18}$F-labeling step further includes diluting at least one of the $^{18}$F solution and the probe precursor with an organic solvent so that, when the $^{18}$F solution and the probe precursor are combined, the total amount of water in the $^{18}$F-labeling solution is in the range of about 0.1 vol % to about 2.0 vol %.

5. The method of claim 1, wherein the at least one phase transfer catalyst is Kryptofix K222.

6. The method of claim 1; wherein the polar aprotic solvent is selected from the group consisting of acetonitrile, tetrahydrofuran ("THF"), dimethylformamide ("DMF"), N methylpyrrolidone ("NMP"), and dioxane.

7. The method of claim 1, wherein the $^{18}$F-labeled probe generated is selected from the group consisting of $^{18}$F FDG, $^{18}$F HX4, $^{18}$F FLT, $^{18}$F MISO, $^{18}$F FAZA, $^{18}$F Fallypride, $^{18}$F FHBG, $^{18}$F FHPG, $^{18}$F-4-fluorobenzaldehyde, $^{18}$F-4-fluoroethylbenzoate, $^{18}$F-4-fluoromethyl benzoate, $^{18}$F-fluoroethylazide, and $^{18}$F-W372.

8. The method of claim 1; wherein the $^{18}$F-labeled probe generated is $^{18}$F-VM4-037.

9. A method for synthesizing an $^{18}$F-labeled probe the method comprising:
 (1) eluting an amount of $^{18}$F with a solution comprising:
  (a) a first solvent comprising a predetermined amount of water and at least one organic aprotic solvent, but no organic protic solvents; and
  (b) at least one labeling reagent comprising $K_2CO_3$, $KHCO_3$, $Cs_2CO_3$, potassium mesylate, potassium oxylate, or tetrabutylammonium bicarbonate; and
  (c) at least one phase transfer catalyst;
 the $^{18}$F eluting as an $^{18}$F solution, wherein a total amount of water in the $^{18}$F solution is in a range of about 0.1 vol % to about 5.0 vol %; and
 (2) diluting the $^{18}$F solution with the organic solvent so as to provide an $^{18}$F-labeling solution having a total amount of water in the range of about 0.5 vol % to about 1.5 vol %;
 (3) using the $^{18}$F solution to perform $^{18}$F-labeling so as to generate the $^{18}$F labeled probe;
 wherein there is no step of drying the $^{18}$F solution starting from a time when the eluting is performed and ending at a time when the $^{18}$F-labeling is performed.

10. A method for synthesizing an $^{18}$F-labeled probe the method comprising:
 (1) eluting an amount of $^{18}$F with a solution comprising:
  (a) a first solvent comprising a predetermined amount of water, no organic protic solvents, and at least one organic aprotic solvent, selected from acetonitrile, tetrahydrofuran ("THF"), dimethylformamide ("DMF"), N methylpyrrolidone ("NMP"), and dioxane; and
  (b) at least one labeling reagent comprising $K_2CO_3$, $KHCO_3$, $Cs_2CO_3$, potassium mesylate, potassium oxylate, or tetrabutylammonium bicarbonate; and
  (c) at least one phase transfer catalyst;
 the $^{18}$F eluting as an $^{18}$F solution, wherein a total amount of water in the $^{18}$F solution is in a range of about 0.1 vol % to about 5.0 vol %;
 (2) diluting the $^{18}$F solution with the organic solvent so as to provide an $^{18}$F-labeling solution having a total amount of water in the range of about 0.1 vol % to about 2.0 vol %;
 (3) using the $^{18}$F solution to perform $^{18}$F-labeling so as to generate the $^{18}$F labeled probe; and
 wherein there is no step of drying the $^{18}$F starting from a time when the eluting is performed and ending at a time when the $^{18}$F-labeling is performed.

11. The method of claim 10, wherein a total amount of water in the $^{18}$F solution is in a range of about 0.5 vol % to about 1.5 vol %.

12. The method of claim 10, wherein the $^{18}$F-labeling further includes diluting at least one of the $^{18}$F solution and the probe precursor with an organic solvent so that, when the $^{18}$F solution and the probe precursor are combined, the $^{18}$F-labeling solution has the total amount of water in the range of about 0.1 vol % to about 2.0 vol %.

13. The method of claim 10, wherein the at least one phase transfer catalyst is Kryptofix K222.

14. The method of claim 10, wherein the $^{18}$F-labeled probe is $^{18}$F FDG, $^{18}$F HX4, $^{18}$F FLT, $^{18}$F MISO, $^{18}$F FAZA, $^{18}$F Fallypride, $^{18}$F FHBG, $^{18}$F FHPG, $^{18}$F-4-fluorobenzaldehyde, 18F-4-fluoroethylbenzoate, $^{18}$F-4-fluoromethyl benzoate, $^{18}$F-fluoroethylazide, or $^{18}$F-W372.

15. The method of claim 10, wherein the $^{18}$F-labeled probe is $^{18}$F-VM4-037.

16. The method of claim 9, wherein the $^{18}$F-labeled probe is $^{18}$F FDG, $^{18}$F HX4, $^{18}$F FLT, $^{18}$F MISO, $^{18}$F FAZA, $^{18}$F Fallypride, $^{18}$F FHBG, $^{18}$F FHPG, $^{18}$F-4-fluorobenzaldehyde, 18F-4-fluoroethylbenzoate, $^{18}$F-4-fluoromethyl benzoate, $^{18}$F-fluoroethylazide, or $^{18}$F-W372.

* * * * *